(12) United States Patent
Rizk et al.

(10) Patent No.: US 9,204,893 B2
(45) Date of Patent: Dec. 8, 2015

(54) SYSTEMS, METHODS AND DEVICES FOR ABLATION, CROSSING, AND CUTTING OF OCCLUSIONS

(75) Inventors: Isa Rizk, San Diego, CA (US); John Fulkerson, Rancho Santa Margarita, CA (US)

(73) Assignee: ReFlow Medical, Inc., San Clemente, CA (US)

( * ) Notice: Subject to any disclaimer, the term of this patent is extended or adjusted under 35 U.S.C. 154(b) by 0 days.

(21) Appl. No.: 12/570,677

(22) Filed: Sep. 30, 2009

(65) Prior Publication Data

US 2011/0054503 A1    Mar. 3, 2011

Related U.S. Application Data

(60) Provisional application No. 61/239,321, filed on Sep. 2, 2009.

(51) Int. Cl.

| A61B 17/3207 | (2006.01) |
|---|---|
| A61B 17/22 | (2006.01) |
| A61M 29/02 | (2006.01) |
| A61M 25/00 | (2006.01) |
| A61F 2/95 | (2013.01) |

(52) U.S. Cl.
CPC ... *A61B 17/3207* (2013.01); *A61B 2017/22094* (2013.01); *A61F 2/95* (2013.01); *A61M 25/0021* (2013.01); *A61M 29/02* (2013.01); *A61M 2025/0042* (2013.01)

(58) Field of Classification Search
CPC .......... A61B 17/320068; A61B 17/3207; A61B 17/32075; A61B 17/3468; A61B 17/3478; A61B 10/0233; A61B 217/22094

USPC .......... 606/170, 185, 127, 159, 167; 604/164.01, 164.06, 164.12, 508
See application file for complete search history.

(56) References Cited

U.S. PATENT DOCUMENTS

| 4,627,841 | A |   | 12/1986 | Dorr |   |
|---|---|---|---|---|---|
| 4,712,547 | A |   | 12/1987 | Bonnet |   |
| 5,053,044 | A |   | 10/1991 | Mueller et al. |   |
| 5,186,712 | A | * | 2/1993 | Kelso et al. | 604/165.03 |
| 5,336,176 | A |   | 8/1994 | Yoon |   |
| 5,376,075 | A | * | 12/1994 | Haughton et al. | 604/158 |
| 5,423,846 | A | * | 6/1995 | Fischell | 606/180 |

(Continued)

FOREIGN PATENT DOCUMENTS

| CA | 2132879 | 3/1995 |
|---|---|---|
| CN | 101288596 | 10/2008 |

(Continued)

OTHER PUBLICATIONS

Wildcat 7F Guidewire Support Catheter—Section 5; 510(K) Summary (21 CFR § 807.92(c)).

(Continued)

*Primary Examiner* — Sarah W Aleman
(74) *Attorney, Agent, or Firm* — Perkins Coie LLP (57) ABSTRACT

Ablation, crossing, and cutting systems, devices and associated methods, including a crossing device, comprising, in combination: a spring-enhanced handle and body configured to controllably extend and retract a blade within a microcatheter for addressing an occlusion within a vessel of a patient to provide improved access for supplemental treatment and reperfusion.

17 Claims, 5 Drawing Sheets

(56) References Cited

U.S. PATENT DOCUMENTS

| | | | |
|---|---|---|---|
| 5,425,718 A * | 6/1995 | Tay et al. | 604/164.11 |
| 5,596,990 A | 1/1997 | Yock et al. | |
| 5,695,469 A | 12/1997 | Segal | |
| 5,724,977 A | 3/1998 | Yock | |
| 5,830,222 A | 11/1998 | Makower | |
| 5,879,305 A | 3/1999 | Yock | |
| 5,935,108 A * | 8/1999 | Katoh et al. | 606/194 |
| 5,938,671 A | 8/1999 | Katoh | |
| 5,972,019 A | 10/1999 | Engelson | |
| 6,066,149 A | 5/2000 | Samson | |
| 6,080,175 A * | 6/2000 | Hogendijk | 606/185 |
| 6,159,198 A | 12/2000 | Gardeski et al. | |
| 6,488,693 B2 * | 12/2002 | Gannoe et al. | 606/167 |
| 6,506,178 B1 | 1/2003 | Schubart | |
| 6,533,753 B1 | 3/2003 | Haarstad | |
| 6,544,247 B1 | 4/2003 | Gardeski et al. | |
| 6,579,302 B2 | 6/2003 | Duerig | |
| 6,663,577 B2 | 12/2003 | Jen | |
| 6,666,847 B2 | 12/2003 | Secrest et al. | |
| 6,786,875 B2 * | 9/2004 | Barker et al. | 604/164.12 |
| 7,320,695 B2 | 1/2008 | Carroll | |
| 7,399,291 B2 | 7/2008 | Vo | |
| 7,749,196 B2 * | 7/2010 | Osborne et al. | 604/164.01 |
| 8,070,762 B2 | 12/2011 | Escudero et al. | |
| 8,202,246 B2 | 6/2012 | Kugler et al. | |
| 8,241,315 B2 * | 8/2012 | Jenson et al. | 606/194 |
| 2001/0000041 A1 | 3/2001 | Selmon et al. | |
| 2001/0031981 A1 | 10/2001 | Evans et al. | |
| 2004/0230219 A1 | 11/2004 | Roucher, Jr. | |
| 2005/0004523 A1 | 1/2005 | Osborne et al. | |
| 2005/0049574 A1 | 3/2005 | Petrick et al. | |
| 2005/0209559 A1 | 9/2005 | Thornton et al. | |
| 2006/0004323 A1 | 1/2006 | Chang | |
| 2006/0167416 A1 * | 7/2006 | Mathis et al. | 604/164.01 |
| 2006/0184186 A1 | 8/2006 | Noone | |
| 2006/0293612 A1 * | 12/2006 | Jenson et al. | 600/585 |
| 2007/0021685 A1 | 1/2007 | Oepen et al. | |
| 2007/0208368 A1 | 9/2007 | Katoh et al. | |
| 2007/0265563 A1 * | 11/2007 | Heuser | 606/194 |
| 2008/0097247 A1 | 4/2008 | Eskuri | |
| 2008/0114390 A1 | 5/2008 | Guinan | |
| 2008/0140101 A1 | 6/2008 | Carley et al. | |
| 2008/0188793 A1 * | 8/2008 | Kozak et al. | 606/159 |
| 2008/0228171 A1 | 9/2008 | Kugler et al. | |
| 2008/0243065 A1 | 10/2008 | Rottenberg et al. | |
| 2008/0249465 A1 | 10/2008 | Ryder et al. | |
| 2008/0294145 A1 | 11/2008 | Eddings et al. | |
| 2009/0093791 A1 | 4/2009 | Heuser | |
| 2009/0159086 A1 | 6/2009 | Hartnick et al. | |
| 2009/0270888 A1 | 10/2009 | Patel | |
| 2010/0125253 A1 | 5/2010 | Olson et al. | |
| 2010/0274270 A1 | 10/2010 | Patel et al. | |
| 2011/0004107 A1 | 1/2011 | Rosenthal et al. | |
| 2011/0034937 A1 | 2/2011 | Mustapha et al. | |
| 2011/0040315 A1 | 2/2011 | To et al. | |
| 2011/0208222 A1 | 8/2011 | Ljahnicky et al. | |
| 2011/0301626 A1 | 12/2011 | To et al. | |
| 2012/0041307 A1 | 2/2012 | Patel et al. | |
| 2012/0046679 A1 | 2/2012 | Patel et al. | |
| 2012/0083810 A1 | 4/2012 | Escudero et al. | |
| 2012/0109171 A1 | 5/2012 | Zeroni et al. | |
| 2012/0253186 A1 | 10/2012 | Simpson et al. | |
| 2013/0006173 A1 | 1/2013 | Alvarez et al. | |

FOREIGN PATENT DOCUMENTS

| | | |
|---|---|---|
| DE | 4434567 A1 | 4/1995 |
| EP | 1205207 A1 | 5/2002 |
| JP | A-2008-504062 | 2/2008 |
| WO | WO-0154588 A1 | 8/2001 |
| WO | WO-2005042080 A1 | 5/2005 |
| WO | WO-2006011970 | 2/2006 |
| WO | WO-2010027843 A1 | 3/2010 |
| WO | WO-2011028203 A1 | 3/2011 |
| WO | WO-2011028632 A1 | 3/2011 |
| WO | WO-2011028665 A2 | 3/2011 |

OTHER PUBLICATIONS

International Search Report and Written Opinion, PCT/US09/055950, Mailed Oct. 14, 2010, Applicant: ReFlow Medical, Inc., 10 pages.
2012 Microcatheter Buyer's Guide, *Endovascular Today*, Dec. 2011, vol. 10, No. 12, pp. 48-51.
International Search Report, PCT/US2010/047170, Mailed May 31, 2011, Applicant: ReFlow Medical, Inc., 5 pages.
2008, Microcatheter's Buyers Guide, *Endovascular Today*, Dec. 2007, vol. 6, No. 12, pp. 106-107.
"BD Vacutainer Push Button Blood Collection Set," Becton, Dickinson and Company, http://www.bd.com/vacutainer/pdfs/VS7024_BD_vacutiner_Push_Button_dc.pdf, Dec. 2007, Franklin Lakes, New Jersey (2 pages).
"BD Vacutainer Safety-Lok Blood Collection Set," Becton, Dickinson and Company, http://www.bd.com/vauctainer/pdfs/safety-lok_bcs_VSS116.pdf, Sep. 2004, Franklin Lakes, New Jersey (4 pages).
Kratchman, Louis B., et al., "Toward Robotic Needle Steering in Lung Biopsy: A Tendon-Actuated Approach." SPIE Medical Imaging, International Society for Optics and Photonics, 2011. 8 pages.
"Introducing the Seeker Steerable Biopsy Needle." PneumRx, Inc. http://www.veranmedical.com/pdf/PneumRx-Coax%20Biopsy%20Needle.pdf. Accessed Jun. 12, 2013. 2 pages.
Non-Final Office Action; Chinese Application No. CN201080049452.9, mailed on Apr. 28, 2014, 10 pages.
Non-Final Office Action; Japanese Application No. 2012527953, mailed on Jun. 23, 2014, 5 pages.
Patent Examination Report No. 1, Australian Application No. PCT/US20102/89659, Date Mailed Oct. 14, 2013, 4 pages.
Extended European Search Report; Application No. EP10814335, mailed Dec. 13, 2013, 6 pages.
International Search Report; PCT/US2009/055950, mailed Apr. 4, 2012, Applicant: Reflow Medical Inc., 6 pages.
International Search Report; PCT/US2010/047170, mailed Apr. 3, 2012, Applicant: Reflow Medical Inc., 8 pages.
European Examination Report; EP10814335.5, mailed Jul. 23, 2015, 5 pages.
Non-Final Office Action; Japanese Application No. 2012527953, mailed on Jun. 29, 2015, 3 pages.
Razavi, Mahmood K. et al., "Forging a Path: An Elegant New Catheter Provides a Winning CTO Solution," Endovascular Today, Aug. 2015, pp. 30-33.
International Search Report, PCT/US2014/052991, mailed Dec. 5, 2014, Applicant: ReFlow Medical, Inc., 16 pages.
Non-Final Office Action; Japanese Application No. 2012527953, mailed on Jun. 23, 2014, 9 pages.
Non-Final Office Action for U.S. Appl. No. 13/648,144, mailed Oct. 27, 2015, 11 pages.

* cited by examiner

SYSTEMS, METHODS AND DEVICES FOR ABLATION, CROSSING, AND CUTTING OF OCCLUSIONS

RELATED APPLICATION

This application claims the full Paris Convention benefit of and priority to U.S. Provisional Patent Application Ser. No. 61/239,321, filed Sep. 2, 2009; and PCT Application Ser. No. PCT/US09/55950, filed on Sep. 3, 2009; the contents of which are incorporated by reference herein in their entirety, as if fully set forth herein.

BACKGROUND

Field

This disclosure relates to systems and apparatus for treating humans via allopathic or surgical intervention, minimally invasive surgical practices, endovascular procedures, percutaneous procedures, and related medical procedures. Specifically, this disclosure relates to systems for addressing vessel lumen-based issues and treatment of occlusions within a body, including those related to peripheral vascular disease states, cardiovascular diseases, cerebrovascular diseases, and others.

SUMMARY

Improved ablation, crossing, and cutting devices and associated systems and methods are disclosed for treatment of occlusions within a body, owing to the paucity of effective devices available clinically, and the longstanding needs in this field of art.

According to embodiments, a crossing device is disclosed, comprising, in combination: a body coupled to a microcatheter at a proximal end of the microcatheter; a handle coupled to a blade at a proximal end of the blade, the blade disposed within a lumen of the microcatheter; wherein a sharpened tip of the blade is configured to advance from a natural position within the lumen of the microcatheter to an extended position beyond a distal end of the microcatheter as the handle is advanced relative to the body.

The crossing device may further comprise a spring configured to compress as the handle is advanced relative to the body; wherein the spring is configured to expand and retract the blade relative to the microcatheter as the handle is released.

The crossing device may further comprise a luer configured to attach to a proximal end of the handle and provide adaptable use of a supplemental treatment device in combination with the crossing device. The luer may be configured to guide a supplemental treatment device to the lumen of the microcatheter or a lumen of the blade. The supplemental treatment device may be at least one of: a guidewire, a PTA balloon, and a stent device.

The tip of the blade may be disposed at a distal end of the blade and is of a rigid material. The tip of the blade may be a hollow, sharpened, everted tip.

The handle and the body may be configured to limit the expansion of the spring and provide the natural position of the blade and further configured to selectively lock the blade in at least one of the natural position and the extended position. The body may further comprise a nose detachable from the body and secured to the microcatheter, such that the microcatheter is selectively removable from the body.

According to embodiments, an improved surgical method for addressing blockage within a vessel is disclosed, comprising, in combination: delivering an apparatus including at least a microcatheter to a desired treatment situs; positioning the microcatheter having at least a blade proximate to a surface of an occlusion, wherein the microcatheter is attached to a body and comprises a lumen; providing the blade within the lumen of the microcatheter to the surface of the occlusion, wherein the blade is attached to a handle; advancing the blade to an extended position by manipulation of the handle relative to the body; and retracting the blade to a natural position by releasing the handle.

The blade may be retracted by a spring between the handle and the body. The method may result in reconfiguration of at least a portion of the occlusion, whereby a different flow condition may be achieved.

The method may further comprise advancing the microcatheter and the blade through a channel created by advancement of the blade to an extended position. The method may further comprise providing a supplemental treatment device to the occlusion through a lumen of the blade. The supplemental treatment device may be at least one of a guidewire, a PTA balloon, and a stent device.

According to embodiments, a kit is disclosed, comprising: a crossing device further comprising: a body coupled to a microcatheter at a proximal end of the microcatheter; a handle coupled to a blade at a proximal end of the blade, the blade disposed within a lumen of the microcatheter; wherein a sharpened tip of the blade may be configured to advance from a natural position within the lumen of the microcatheter to an extended position beyond a distal end of the microcatheter as the handle is advanced relative to the body; and directions for use.

The kit may further comprise a supplemental treatment device configured to be advanced within the lumen of the microcatheter. The kit may further comprise a luer disposed at a proximal end of the handle and configured to guide the supplemental treatment device into the lumen of the microcatheter. The supplemental treatment device may be at least one of: a guidewire, a PTA balloon, and a stent device.

A system for addressing obstructions within lumens, comprising, in combination: a body coupled to a microcatheter at a proximal end of the microcatheter; a handle coupled to a blade at a proximal end of the blade, the blade disposed within a lumen of the microcatheter; a luer configured to attach to a proximal end of the handle and provide adaptable use of a supplemental treatment device in combination with the crossing device; a spring configured to compress as the handle is advanced relative to the body; wherein a tip of the blade may be configured to advance from a natural position within the lumen of the microcatheter to an extended position beyond a distal end of the microcatheter as the handle is advanced relative to the body; wherein the spring may be configured to expand and retract the blade relative to the microcatheter as the handle is released.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

The present inventors have discovered that treatment of conditions, including chronic total occlusions, remain challenged by the paucity of extent devices. Namely, surgeons require improved apparatus to impact, address, and ameliorate occlusions by thrombi, emboli, and other obstructions in real time during procedures.

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, mechanical, electrical, functional, and other changes may be made without departing from the scope of the present disclosure. The following detailed description is, therefore, not to be taken in a limiting sense, and the scope of the present disclosure is defined only by the appended claims. As used in the present disclosure, the term "or" shall be understood to be defined as a logical disjunction and shall not indicate an exclusive disjunction unless expressly indicated as such or notated as "xor."

The inventors of the present disclosure have invented and reduced to practice improved systems, comprised of devices and methods for ablating, crossing, or cutting an occlusion including known constraints of managing fluid-flow and other access issues within a body, particularly in the lumen of vessels. The devices and methods discussed herein may be employed for medical treatment and in conjunction with other devices and methods for medical treatment, as known to those skilled in the art.

Where a patient is indicated for certain treatment, monitoring, or intervention or suffers from a disease, a lumen of a blood vessel or other fluid-bearing vessel may become occluded. For example, a chronic total occlusion ("CTO") or other partial or total obstruction of a blood vessel may occur or be the result of a thrombus, an embolism, atherosclerosis, or other disease that results in a blockage, restriction, or occlusion of fluid flow within a body. Often, during procedures, situations arise requiring immediate intervention, such as to address a CTO.

Where treatment of an occlusion by endovascular procedure is desired, medical professionals may attempt endovascular surgical procedures. Endovascular procedures include angioplasty procedures, stent placement, various scope procedures, and plethoric diagnostic, intermediary and interlocutory clot addressing schemes, which may include temporarily or permanently emplaced devices.

An occlusion may include a fibrous cap, composed of lipids, endothelial cells, macrophages, smooth muscle cells, foam cells, connective tissue, and other vascular materials. An occlusion may include calcification, such that the occlusion becomes hardened. Under these conditions, various endovascular procedures including thrombectomy, angioplasty, stent placement, retrieval of an obstruction, and others may be complicated or prevented by the difficulty or inability to penetrate the occlusion. For example, such procedures may require at least partial penetration of an occlusion before the procedure may be commenced or completed. Often, establishing some degree of reperfusion is critical.

According to embodiments, as shown in FIGS. 1A, 1B, 2A, and 2B, crossing device 1 may include body 13, microcatheter 21, handle 12, and blade 16. According to embodiments, crossing device 1 allows for a handheld mechanical penetration of an occlusion. Surgeons and interventionalists have expressed ongoing needs for devices leveraging their "hand" or feel for manipulating devices in situ.

Figure 1A:
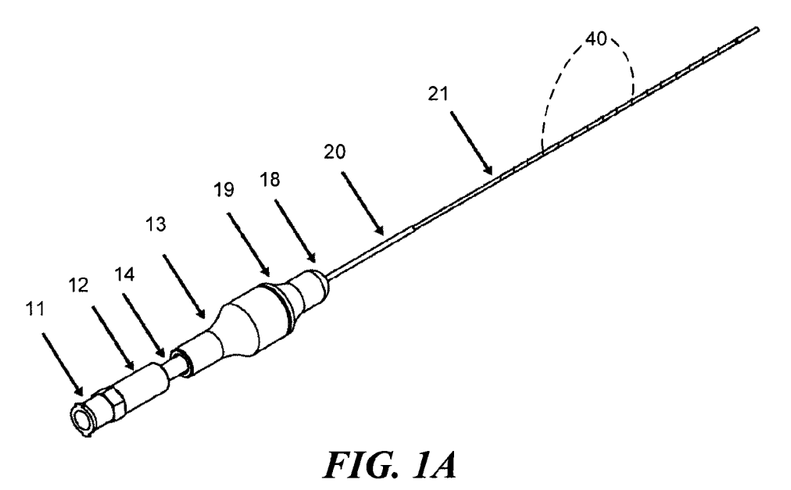
FIG. 1A is a schematic view of an embodiment of a crossing device in a natural position, according to embodiments of the present disclosure.
Figure 1B:
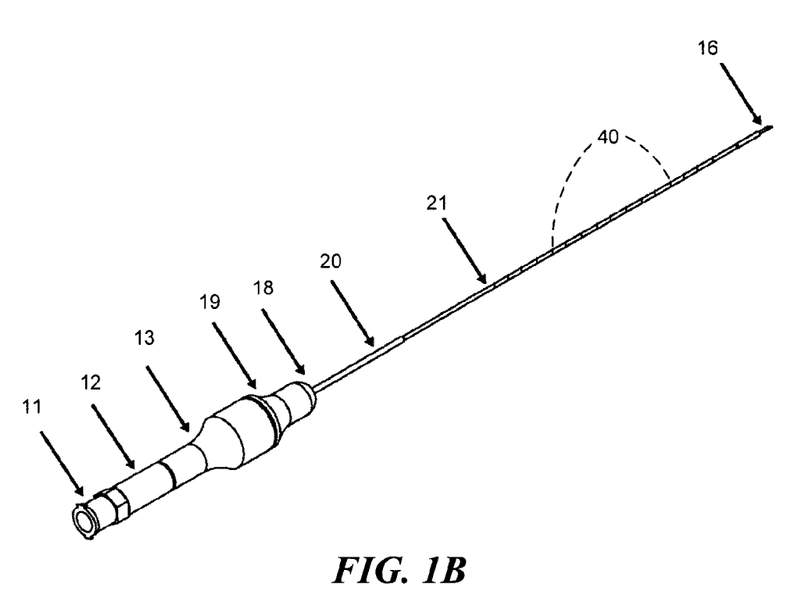
FIG. 1B is a schematic view of an embodiment of a crossing device in an extended position, according to embodiments of the present disclosure.
Figure 2A:
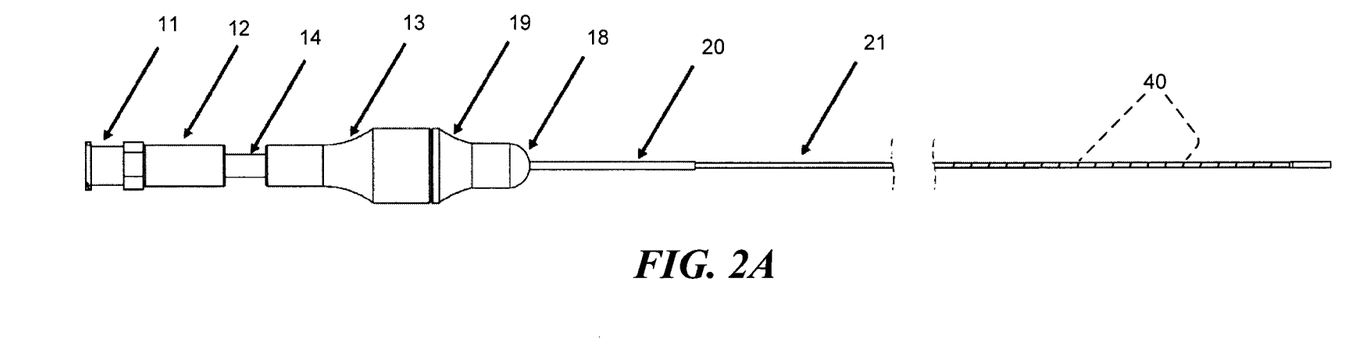
FIG. 2A is a schematic view of an embodiment of a crossing device in a natural position, according to embodiments of the present disclosure.
Figure 2B:
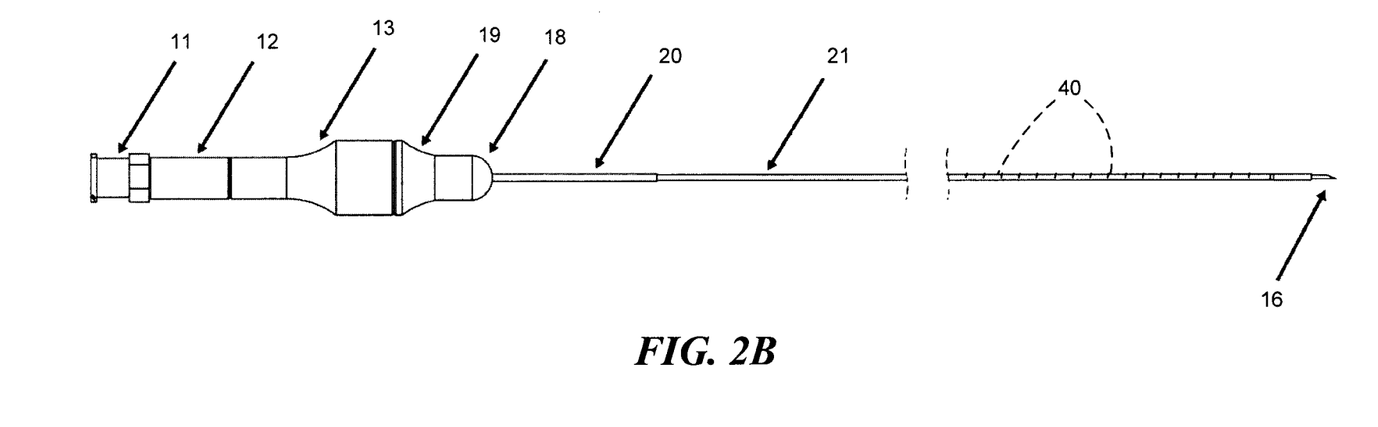
FIG. 2B is a schematic view of an embodiment of a crossing device in an extended position, according to embodiments of the present disclosure.

According to embodiments, body 13 may be attached to microcatheter 21, and handle 12 may be attached to blade 16, such that handle 12 is moveable relative to body 13, and movement of handle 12 relative to body 13 causes advancement and retraction of blade 16 along the inner portion of microcatheter 21. FIGS. 1A and 2A show crossing device 1 in a natural position, with handle 12 and blade 16 retracted; FIGS. 1B and 2B show crossing device 1 in an extended position, with handle 12 and blade 16 extended.

Figure 3:
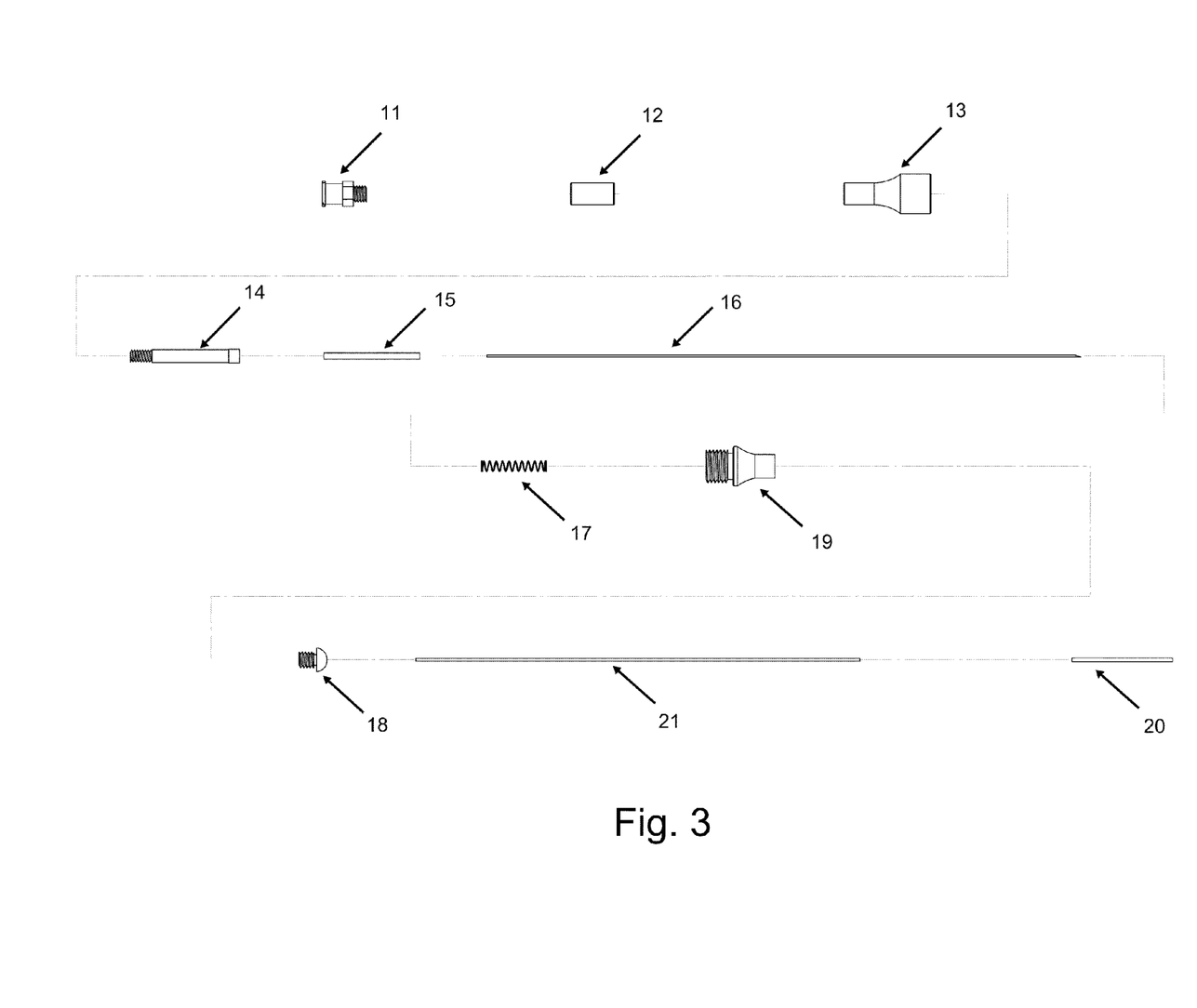
FIG. 3 is an exploded view of an embodiment of a crossing device, according to embodiments of the present disclosure.
Figure 4:
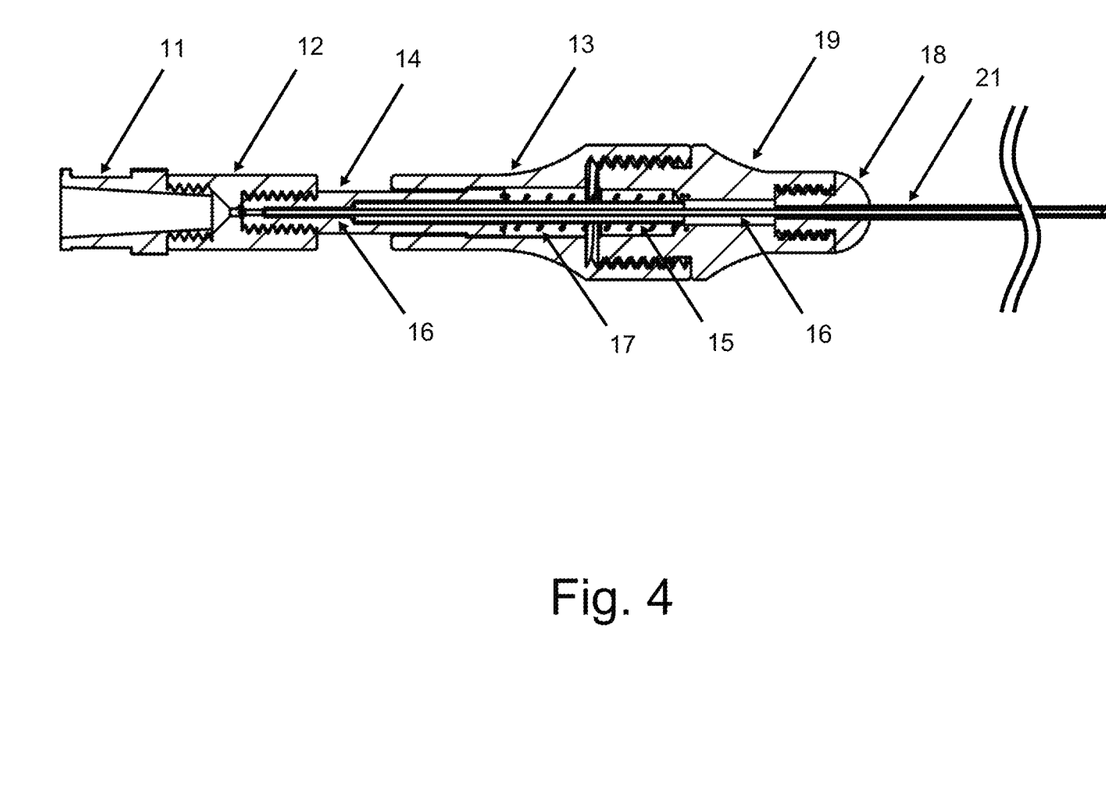
FIG. 4 is a cross-sectional view of an embodiment of a crossing device, according to embodiments of the present disclosure.

According to embodiments, handle 12 may include or be combined with one or more of luer 11, plunger rod 14, hypo support 15, and blade 16. For example, as shown in FIGS. 3 and 4, handle 12, luer 11, plunger rod 14, hypo support 15, and blade 16 may be combined to form an integrated unit. One or more interfaces (e.g., threading, etc.) or fixations (e.g., adhesive, epoxy, etc.) may be provided to combine said components.

According to embodiments, body 13 may include or be combined with one or more of nose guide 19, nose 18, heat shrink 20, and microcatheter 21. For example, as shown in FIGS. 3 and 4, body 13, nose guide 19, nose 18, heat shrink 20, and microcatheter 21 may be combined to form an integrated unit. One or more interfaces (e.g., threading, etc.) or fixations (e.g., adhesive, epoxy, etc.) may be provided to combine said components.

According to embodiments, spring 17 may be disposed between at least a portion of handle 12 and at least a portion of body 13. For example, as shown in FIG. 4, spring 17 extends between plunger rod 14—which is attached to handle 12—and nose guide 19—which is attached to body 13.

According to embodiments, spring 17 may tend to separate handle 12 from body 13 by way of elastic expansion. Handle 12 and body 13 may be configured to set a limit on the separation. For example, as shown in FIGS. 3 and 4, plunger rod 14 may include a flange that contacts a portion of body 13 to prevent travel along the axis beyond a certain point.

According to embodiments, nose 18 may be separate from and attachable to nose guide 19. Nose 18 may be fixably attached to microcatheter 21 and removably attached to nose guide 19, such that a microcatheter may be exchanged by removing nose 18. Such an option avoids the need to replace an entire system for need of a new microcatheter.

According to embodiments, crossing device 1 may facilitate use of a guidewire. Blade 16 may be configured with a hollow inner portion to allow a guidewire to be advanced from a proximal end of blade 16 to a distal end of blade 16. A guidewire lumen within blade 16 may be configured to accommodate any guidewire used for general vascular surgical procedures, such that a separate or distinct guidewire is not required for operation of crossing device 1. Such technology is known in the art, and incorporated herein by reference are the following U.S. patent applications and publications: U.S. Pat. No. 6,066,149, U.S. Pat. No. 5,972,019, U.S. Pat. No. 5,695,469, U.S. Pat. No. 6,506,178, U.S. Pat. No. 6,533,753, U.S. Pat. No. 6,579,302, U.S. Pat. No. 6,663,577, U.S. Pat. No. 7,399,291, U.S. Pat. No. 5,879,305, U.S. Pat. No. 5,724,977, U.S. Pat. No. 5,596,990, U.S. Publication No. 2004/0230219, U.S. Publication No. 2005/0209559, U.S. Publication No. 2007/0265563, U.S. Publication No. 2005/0049574, U.S. Publication No. 2006/0184186, U.S. Publication No. 2001/0031981, U.S. Publication No. 2007/0208368, U.S. Publication No. 2007/0021685, U.S. Publication No. 2008/0097247, U.S. Publication No. 2008/0140101, U.S. Publication No. 2008/0114390, U.S. Publication No. 2008/0228171, and U.S. Publication No. 2008/0249465.

According to embodiments, a luer 11 may be configured to interface with handle 12, as shown in FIGS. 3 and 4. Luer 11 may be a detachable hub/luer device configured to direct devices to microcatheter 21. Luer 11 may facilitate use of a support catheter, PTA balloon catheter, guidewire, or another lumen-configured or catheter-based supplemental treatment device to be exchanged with components of crossing device 1 during use, without removal of crossing device 1 from a patient. Such a configuration provides the ability to operate crossing device 1 in tandem or in sequence with other devices intended to deliver treatment to the same or nearby location.

According to embodiments, devices advanced within the lumen of blade 16 or otherwise provided through luer 11 may be operated, manipulated, and moved either along with or independent of handle 12, body 13, or their associated attached components.

Figure 5A:
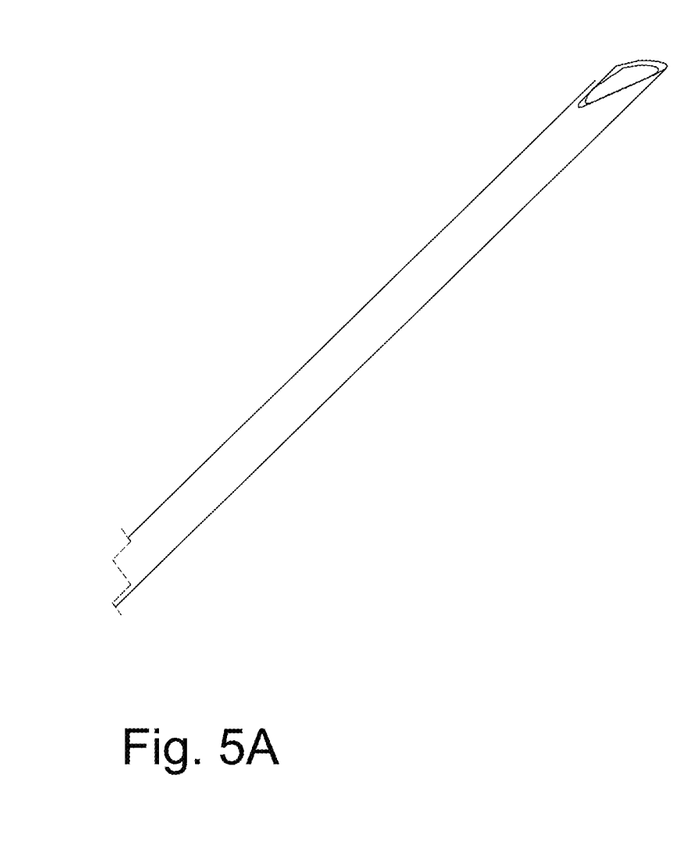
FIG. 5A is a schematic view of an embodiment of a blade of a crossing device, according to embodiments of the present disclosure.
Figure 5B:
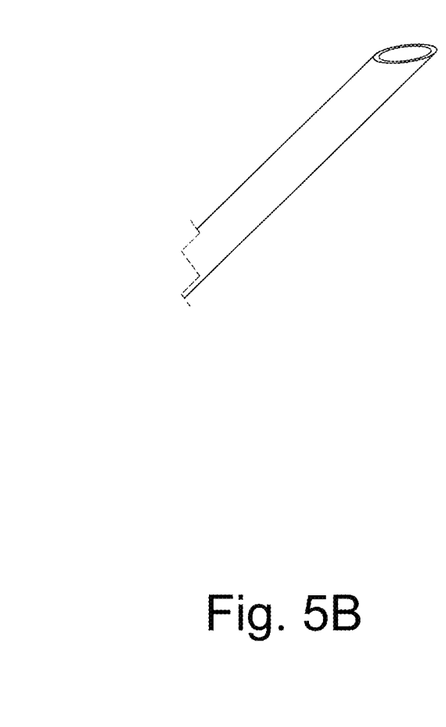
FIG. 5B is a schematic view of an embodiment of a blade of a crossing device, according to embodiments of the present disclosure.

According to embodiments, blade 16 may be configured to penetrate an occlusion upon contact with the occlusion. The distal end of blade 16 may include one of a variety of shapes to facilitate addressing the occlusion. Examples are shown in FIGS. 5A and 5B. For example, blade 16 may include an everted end, an end with a sharpened tip, a concave end, a convex end, a coring tip, or other geometry to address an occlusion. Blade 16 may be hollow or solid.

According to embodiments, microcatheter 21 and blade 16 may provide sufficient flexibility to provide trackability within vessels of a patient. Microcatheter 21 and blade 16 may also provided sufficient rigidity to adequately transfer translational and rotational forces to be responsive at a distal end to a user located at a proximal end. According to embodiments, a tip at a distal end section of blade 16 may be relatively rigid, to provide a force of impact to an occlusion upon extension of the same.

According to embodiments, blade 16 may be configured to provide rotational motion at the point of deployment (e.g., at or near the distal end of crossing device 1). For example, as a user provides torque to handle 12, the torque may be translated along blade 16 to the distal end of blade 16. A torque provided at the distal end may improve treatment of the occlusion. The torque may be applied and translated before, during, or after extension of blade 16 beyond the distal end of microcatheter 21 and penetration of the occlusion.

According to embodiments, blade 16 may be configured to automatically rotate as it advances longitudinally relative to microcatheter 21. For example, threading may be provided about the axis along which blade 16 travels, such that travel of blade 16 along the axis also results in rotation of blade 16. For example, microcatheter 21 may be provided on at least a portion of its inner surface with threading, channels, or other guiding members 40 to govern the manner in which blade 16 is advanced and retracted therein. Blade 16 may be provided with threading or other features to complement the guiding members of the axis along which blade 16 travels. For example, at least a portion of blade 16 may have a substantially spiral geometry adapted to interface with a complementary threading of microcatheter 21.

According to embodiments, blade 16 may be configured to penetrate or cross a section of an occlusion. According to embodiments, at least a portion of the occlusion may be captured or enclosed by features of blade 16. For example, ridges, protrusions, edges, and spiral geometries may be provided at the distal end of blade 16 to capture or enclose at least a portion of the occlusion that is penetrated by blade 16. Subsequently, blade 16 may be retracted, whereby at least a portion of the occlusion is removed by blade 16.

For example, where blade 16 includes a substantially spiral geometry, blade 16 may be advanced relative to microcatheter 21 with simultaneous longitudinal and rotational motion, whereby the spiral geometry captures at least a portion of the occlusion. Subsequently, blade 16 may be retracted longitudinally, whereby the portions of the occlusion are maintained within the spiral geometry. For example, blade 16 may be retracted with microcatheter 21. The foregoing may result in a path within the occlusion which may be the object of further operations, such as by the same device or others, or may be a path that at least partially restores a flow of blood and reperfusion through the occlusion.

According to embodiments, blade 16 may be configured to be entirely or almost entirely disposed within microcatheter 21 at its distal end when crossing device 1 is in a natural position, as shown in FIGS. 1A and 2A, and to be somewhat extended beyond the distal end of microcatheter 21 when crossing device 1 is in an extended position, as shown in FIGS. 1B and 2B.

According to embodiments, blade 16 may be configured to lock relative to microcatheter 21 when in a natural position or an extended position. Mechanisms to selectively or automatically lock and unlock blade 16 may be provided and may be operable by a user located at a proximal end of crossing device 1 to activate or deactivate said mechanisms.

According to embodiments, crossing device 1 may be configured as either an "over the wire" device (see FIG. 4) or a "rapid exchange" device (not shown). For example, supplemental devices may be configured to interface with crossing device 1 in a rapid exchange configuration. Crossing device 1 may include at least one lumen to accommodate a supplemental device to be used in conjunction with other components of crossing device 1. For example, a rapid exchange lumen may entry access at or near a proximal end of crossing device 1 and may extend to the distal end of crossing device 1 (e.g., the distal end of microcatheter 21).

According to embodiments, crossing device 1 may be used to address an occlusion. The distal end of crossing device 1, including a portion of microcatheter 21, blade 16, or a guidewire, may be brought to the location of an occlusion. For example, the guidewire may first be brought to the occlusion, followed by microcatheter 21 and blade 16. Blade 16 may be extended beyond the distal end of microcatheter 21 by operation of handle 12, as disclosed herein. As the occlusion is penetrated, increased advancement of microcatheter 21, blade 16, or a guidewire may be provided. Increased advancement of microcatheter 21, blade 16, or a guidewire may provide a improved position of the same to continue the crossing procedure in iterative steps. The process may be repeated in successive steps until the occlusion is crossed as desired.

According to embodiments, a method for causing blade 16 to penetrate an occlusion is disclosed. According to embodiments, microcatheter 21 may be brought to an occlusion, such as a heavily calcified lesion or other obstruction, as discussed herein. Blade 16 may be advanced by crossing device 1 such that it penetrates the occlusion. Blade 16 may retract when handle 12 is released, by the function of spring 17.

According to embodiments, the above described steps may be repeated as desired. For example, the above described steps may be repeated until the occlusion is entirely breached or until sufficient access is provided for other devices to act upon the occlusion. For example, a PTA balloon, stent device, or other catheter-based supplemental treatment device may operate within a channel created by operation of crossing device 1.

According to embodiments, the method and use of crossing device 1 may provide increased perfusion of fluid flow through the channel created by crossing device 1. The increased perfusion may provide improved conditions to facilitate breakdown of the occlusion, such that perfusion alone or in combination with other methods may remove threats presented by the occlusion.

According to embodiments, variations on embodiments may be made to provide customizable use and performance characteristics of crossing device 1. For example, spring 17 may be omitted such that handle 12 may travel relative to body 13 along the axis within certain limitations, such that the user may selectively and manually advance and retract blade 16 relative to microcatheter 21.

According to embodiments, crossing device 1 may be configured to allow blade 16 to be extended in a natural position and retracted based on action taken by a user (not shown). The configuration shown in FIG. 4 may be modified such that spring 17 is located such that its tendency toward elastic expansion causes handle 12 to be advanced toward body 13. In such a configuration, retraction of handle 12 may compress spring 17, such that release of handle 12 causes advancement of blade 16 toward or beyond the distal end of microcatheter 21.

According to embodiments, crossing device 1 may include two springs to provide novel use and performance characteristics (not shown). For example, one spring may tend toward extension of blade 16, and another spring may tend toward retraction of blade 16. Blade 16 may be configured such that the distal tip of blade 16 is in a desired location when equilibrium between the two springs is achieved in a natural position. A user may selectively advance or retract blade 16 by operation of handle 12, and release for blade 16 to allow release of any energy stored in the springs, with the blade 16 eventually reaching equilibrium in a natural position.

According to embodiments, a kit of parts is disclosed. One or more kits of parts can be envisioned by the person skilled in the art, the kits of parts including at least one component disclose herein and configured to perform at least one of the methods herein disclosed. Likewise, directions for use ("DFU") are included and the device may be part of a surgical tray or other packaged accessory set for surgeries. The kit may be a sub-component of a surgical tray.

While the method and agent have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A crossing device, comprising:
a body coupled to a microcatheter at a proximal end of the microcatheter;
a plunger rod, wherein the body defines a proximal recess into which a portion of a plunger is slidably received;
a handle affixed to a cutting blade at a proximal end of the blade, wherein the cutting blade has a generally constant diameter along its length and comprises a sharpened cutting surface defined by a beveled tip at a distalmost end of the cutting blade,
wherein the cutting blade is disposed within a lumen of the microcatheter, and the microcatheter and cutting blade are flexible to provide trackability within vessels of a patient, and wherein the cutting blade is sized and shaped to receive a guidewire for intravascular delivery to a target treatment site within a blood vessel of the patient, and further wherein the cutting blade is configured to move axially and rotationally relative to the microcatheter;
a spring,
wherein the spring is configured to compress to advance the sharpened cutting surface of the cutting blade axially outward from a natural position within the lumen of the microcatheter to an extended position beyond a distal end of the microcatheter as the handle is advanced distally relative to the body, and
wherein the spring is configured to expand to axially retract the cutting blade from the extended position toward the natural position within the lumen of the microcatheter as the handle is moved proximally; and
a luer configured to be attached to a proximal end of the handle, wherein the luer is configured to facilitate use of a supplemental treatment device in combination with the crossing device,
wherein the body, handle, plunger rod, cutting blade, microcatheter, spring, and luer comprise an integrated unit adapted to remain together throughout operation of the crossing device within the patient.

2. The crossing device of claim 1 wherein the luer is configured to guide a supplemental treatment device to the lumen of the microcatheter.

3. The crossing device of claim 1 wherein the luer is configured to guide a supplemental treatment device to a lumen of the cutting blade.

4. The crossing device of claim 1 wherein the supplemental treatment device comprises at least one of the following: a guidewire, a PTA balloon, and a stent device.

5. The crossing device of claim 1 wherein the tip of the cutting blade comprises a rigid material.

6. The crossing device of claim 1 wherein the tip of the cutting blade comprises a hollow, sharpened, everted tip.

7. The crossing device of claim 1 wherein the handle and the body are configured to limit the expansion of the spring and provide the natural position of the cutting blade, and wherein the handle is further configured to selectively lock the cutting blade in at least one of the natural position and the extended position.

8. The crossing device of claim 1 wherein the body of the crossing device further comprises a nose detachable from the body and releasably secured to the microcatheter, and wherein the microcatheter is selectively removable from the body.

9. The crossing device of claim 1 wherein the lumen of the microcatheter further comprises guiding members configured to provide torque to the cutting blade as the cutting blade is advanced from the natural position to the extended position.

10. The crossing device of claim 1 wherein the tip of the cutting blade comprises a concave end.

11. The crossing device of claim 1 wherein the tip of the cutting blade comprises a convex end.

12. The crossing device of claim 1 wherein the tip of the cutting blade comprises a coring tip.

13. The crossing device of claim 1 wherein the crossing device is configured as a rapid exchange device.

14. The crossing device of claim 1, further comprising a nose guide, a nose, and a heat shrink portion, and wherein the integrated unit further comprises the nose guide, nose, and heat shrink portion.

15. The crossing device of claim 1 wherein the handle and body comprise a handle assembly, and wherein the spring is disposed between the handle and the body of the handle assembly.

16. The crossing device of claim 1 wherein the plunger rod is attached to the handle, and wherein the spring is integral with and extends between the plunger rod and a nose guide attached to the body.

17. A crossing device for treating an obstruction within a blood vessel, the crossing device comprising:
a flexible elongated shaft having a proximal portion, a distal portion, and a lumen extending therethrough;
a flexible cutting blade slidably disposed within the lumen of the flexible shaft and configured to move axially and rotationally relative to the flexible shaft, wherein the cutting blade is sized and shaped to receive a guidewire for intravascular delivery to a treatment site within the blood vessel at least proximate to the obstruction, and further wherein the cutting blade has a generally constant diameter along its length and comprises a sharpened cutting surface defined by a beveled tip at a distalmost end of the cutting blade; and
a handle assembly comprising a body, a handle, and a plunger rod therebetween, wherein a distal portion of the body is coupled to the proximal portion of the flexible shaft and a proximal portion of the handle is connected to a proximal portion of the cutting blade, and wherein the body comprises a proximal recess into which a portion of the plunger rod is slidably disposed, and further wherein the handle is axially and rotationally movable about the flexible shaft, wherein the proximal portion of the flexible shaft is contained within the body and the proximal portion of the cutting blade is contained within the handle, wherein during operation of the crossing device— axial movement of the handle in a distal direction advances the sharpened cutting surface of the cutting blade from a first natural position within the lumen of the flexible shaft to a second extended position beyond a distal end of the flexible shaft, and axial movement of the handle in a proximal direction retracts the cutting blade from its second extended position to its first natural position within the lumen of the flexible shaft.

\* \* \* \* \*

UNITED STATES PATENT AND TRADEMARK OFFICE
CERTIFICATE OF CORRECTION

PATENT NO. : 9,204,893 B2
APPLICATION NO. : 12/570677
DATED : December 8, 2015
INVENTOR(S) : Isa Rizk et al.

It is certified that error appears in the above-identified patent and that said Letters Patent is hereby corrected as shown below:

On the title page, item (30) insert -- PCT Application No. PCT/US09/55950 filed on 09/03/2009 -- under Foreign Application Priority Data, therefor.

On the page 2, in column 2, item (56) under "Other Publications", line 12, delete "vacutiner" and insert -- vacutainer --, therefor.

On the page 2, in column 2, item (56) under "Other Publications", line 15, delete "vaucutainer" and insert -- vacutainer --, therefor.

On the page 2, in column 2, item (56) under "Other Publications", lines 28-29, delete "PCT/US20102/89659," and insert -- PCT/US2010/289659. --, therefor.

In the specification

In column 5, line 51, delete "provided" and insert -- provide --, therefor.

Signed and Sealed this
Third Day of May, 2016

Michelle K. Lee
*Director of the United States Patent and Trademark Office*